Figure 1:
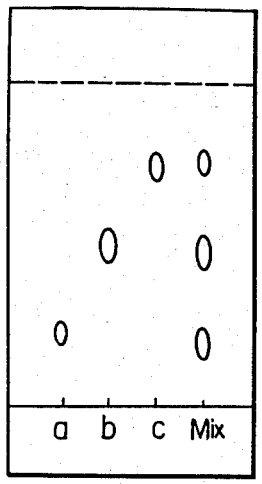

United States Patent [19]

Nagata

[11] Patent Number: 4,508,624

[45] Date of Patent: Apr. 2, 1985

[54] CERAMIC BODY FOR CHROMATOGRAPHY AND PROCESS FOR PREPARATION THEREOF

[75] Inventor: Koichi Nagata, Sendai, Japan

[73] Assignee: Kyoto Ceramic Co., Ltd., Kyoto, Japan

[21] Appl. No.: 445,020

[22] Filed: Nov. 26, 1982

Related U.S. Application Data

[62] Division of Ser. No. 191,388, Sep. 29, 1980, abandoned.

[51] Int. Cl.³ .............................................. B01D 15/08
[52] U.S. Cl. ........................................ 210/658; 55/67; 55/386; 210/198.3
[58] Field of Search ............... 210/198.2, 198.3, 656, 210/658; 55/67, 386

[56] References Cited

U.S. PATENT DOCUMENTS 2,723,756 11/1955 Miller et al. ................. 210/198.2
3,839,205 10/1974 Okumura et al. ............. 210/198.3
4,348,296 9/1982 Bauman ............................ 55/67

Primary Examiner—John Adee
Attorney, Agent, or Firm—Spensley Horn Jubas & Lubitz

[57] ABSTRACT

Disclosed is a ceramic body for chromatography, which consists of a calcined molded body of alumina particles composed mainly of α-alumina, preferably containing a minor amount of γ-alumina, and which has a narrow pore size distribution range.

This ceramic body has no substantial adsorbing property and therefore, when it is used for use like to thin layer chromatography or gas chromatography, the tailing phenomenon is not caused to occur at all and a high separating capacity can be obtained stably.

4 Claims, 8 Drawing Figures

CERAMIC BODY FOR CHROMATOGRAPHY AND PROCESS FOR PREPARATION THEREOF

This is a division of application Ser. No. 191,388, filed on Sept. 29, 1980, now abandoned.

This invention relates to a ceramic body for chromatography consisting of a calcined molded body of α-alumina particles. More particularly, the invention relates to a ceramic body which exerts a high and stable separating capacity without substantial occurrence of the tailing phenomenon when it is used for use like to thin layer chromatography or gas chromatography.

Chromatography is broadly used in the fields of biochemistry, manufacture of agricultural chemicals, manufacture of medicines and other various chemical industries as a process in which a sample is separated to the respective components by utilizing adsorption and/or distribution.

The chromatography heretofore adopted in these fields is roughly divided into two types, that is, the adsorption type and distribution type. Thin layer chromatography is a typical instance of the chromatography utilizing the principles of both the adsorption type and distribution type, and a typical instance of the chromatography utilizing the principle of the distribution type is liquid chromatography. In the thin layer chromatography, a mixture formed by kneading an inorganic or organic adsorbent such as silica gel, alumina or polyamide with a binder, water and other appropriate components with the use of a mixing solvent is coated in the form of a thin layer on a plate-like support such as a glass sheet, a synthetic resin sheet or a metal sheet, the coated mixture is dried under predetermined conditions, an unknown sample is dropped on one end of the thin layer, the lower end or upper end of the plate-like support is dipped in the solvent while the solvent is being evaporated, and after a certain developing time, adsorption and separation of the sample are repeated while the solvent is passed through the thin layer by the capillary phenomenon. By utilizing this phenomenon of the repeated adsorption and separation of the sample, the unknown sample is separated and analyzed.

In the thin layer chromatography, an expensive equipment for formation of a thin layer, such as an applicator, must be used and a considerable skill is necessary for forming a thin layer by using such equipment. Furthermore, a thin layer having a uniform thickness can hardly be obtained. If the thickness of the thin layer is not uniform, attainment of uniform development is very difficult and the result of development lacks reliability and reproducibility. Moreover, even if thin layers are composed of the same material, the activity differs depending on the degree of drying of the adsorbent. Still further, it is very difficult to prepare a number of thin layers continuously, and since a thin layer is formed on a glass substrate or the like by coating, the thin layer is readily peeled by vibration or the like during transportation. Thus, the conventional technique of thin layer chromatography includes various defects.

The liquid chromatography where a substance having a large distribution coefficient is separated and eluted out preferentially is a typical instance of the distribution type chromatography. More specifically, it is necessary to inject a minute amount of a liquid sample into a carrier liquid before a column against the pressure of the carrier liquid (for example, 300 atmospheres) promptly and precisely. In the conventional piercing cap technique using a piston type injection mechanism for the injection, since the inner pressure of the carrier liquid is high, the reproducibility is not always good. Moreover, different materials should be chosen and used for piercing caps according to the intended object of chromatography. Furthermore, when a fine tube of the injection device is introduced into the carrier liquid, a shock pressure is generated because of the non-compressibility of the carrier liquid and this shock pressure is transmitted to the column and detector, and the analysis process is susceptively influenced. In such liquid chromatography, the amount to be developed at one time is small and if the sample is not diluted, the separation capacity is degraded. Therefore, the liquid-phase chromatography is defective in that it takes a long time to separate and collect the sample in an amount necessary for analysis or the like. Furthermore, it is difficult to pack the stationary layer uniformly in a column and commercially available products are very expensive. Moreover, the liquid chromatography is disadvantageous in that detection must be conducted on separation and collection by such means as ultraviolet analysis or refractive index analysis and the entire equipment system becomes voluminous, in that the equipment system must be washed sufficiently before and after separation and collection.

As will be apparent from the foregoing illustration, the conventional chromatography of either the adsorption type or the distribution type involves various defects with respect to the separation capacity and the operation procedures.

In gas chromatography, a gaseous sample or gasified liquid or solid sample is passed through a tube uniformly packed with a filler and thus developed by means of a carrier gas and the sample is separated into respective components. This gas chromatography is roughly divided into gas-solid chromatography where a solid power having an adsorbing capacity is used as the filler and the respective components are separated by utilizing the difference of the adsorbing property and gas-liquid chromatography where a lowly volatile liquid or a solid to be liquified at the application temperature is used as the filler and the respective components are separated by utilizing the difference of the solubility.

Celite or the like having no adsorbing activity is ordinarily used as a carrier of the stationary phase in the above-mentioned gas-liquid chromatography, and conventional alumina cannot be used for this purpose because the adsorbing activity is very high and tailing is readily caused.

According to this invention, there is provided a ceramic body for chromatography which have chemical structure and characteristics quite different from alumina heretofore used as the adsorbing medium or stationary phase in chromatography.

More specifically, in accordance with this invention, there is provided a ceramic body for chromatography, which consists of a calcined and molded body of crystalline alumina particles composed mainly of α-alumina and which has a narrow pore size distribution range.

Since the ceramic body for chromatography according to this invention has no substantial adsorbing property, the tailing phenomenon is not substantially caused when materials are separated, and the high separation capacity can be attained very stably.

Still further, this ceramic body for chromatography can be provided very easily at a low cost only by molding and calcining alumina particles composed mainly of α-alumina. Furthermore, the ceramic body for chromatography according to this invention is very excellent in the mechanical strength, the easiness in handling and the adaptability to the analysis operation.

Figure 2:
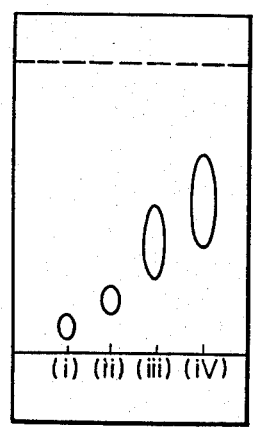
Figure 3:
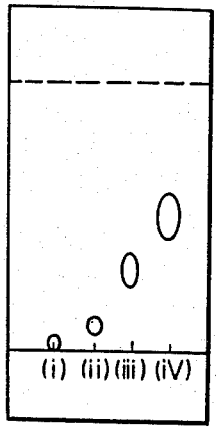
Figure 4:
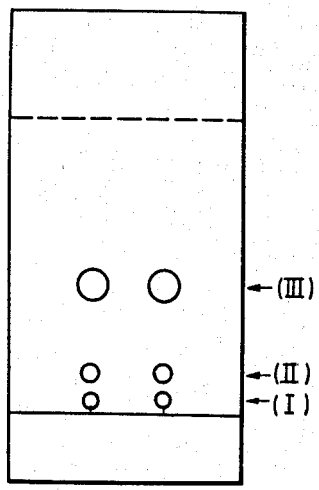
Figure 5:
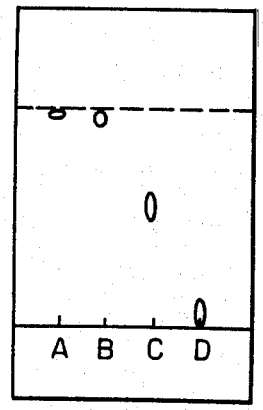
Figure 6:
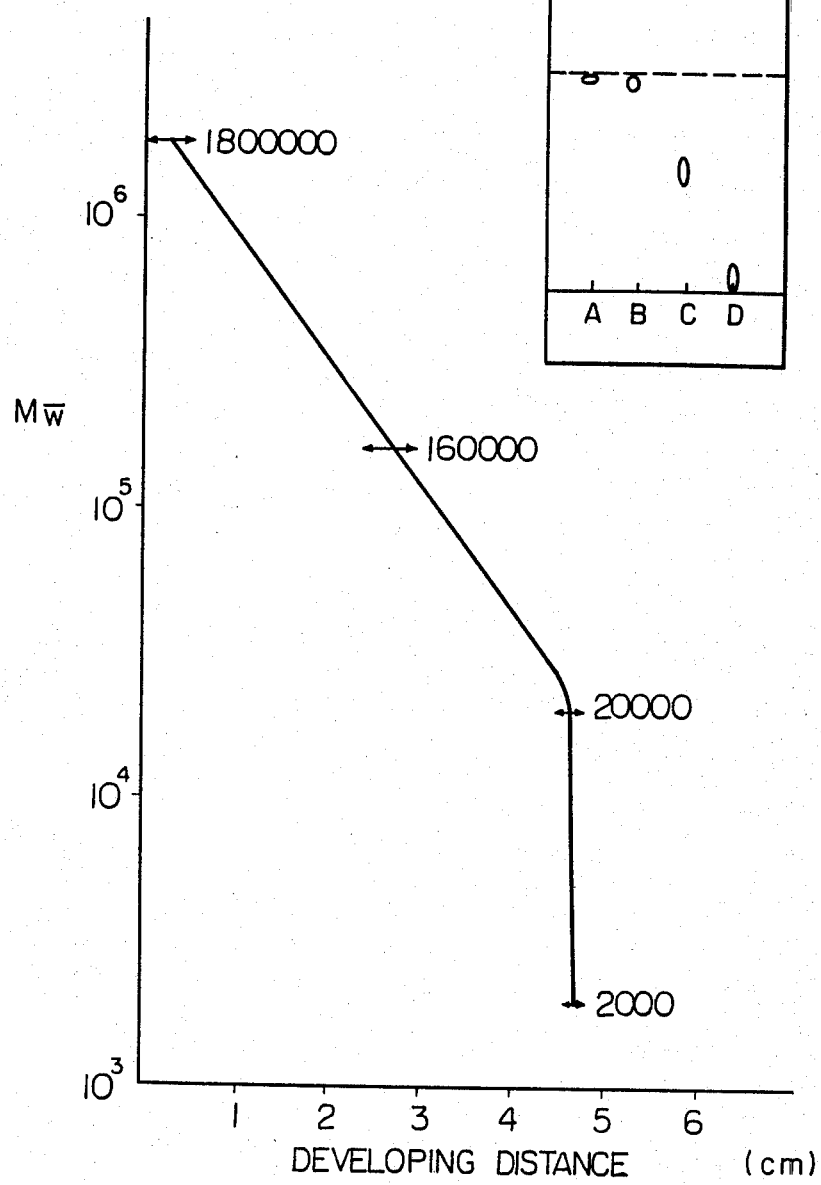
Figure 8:
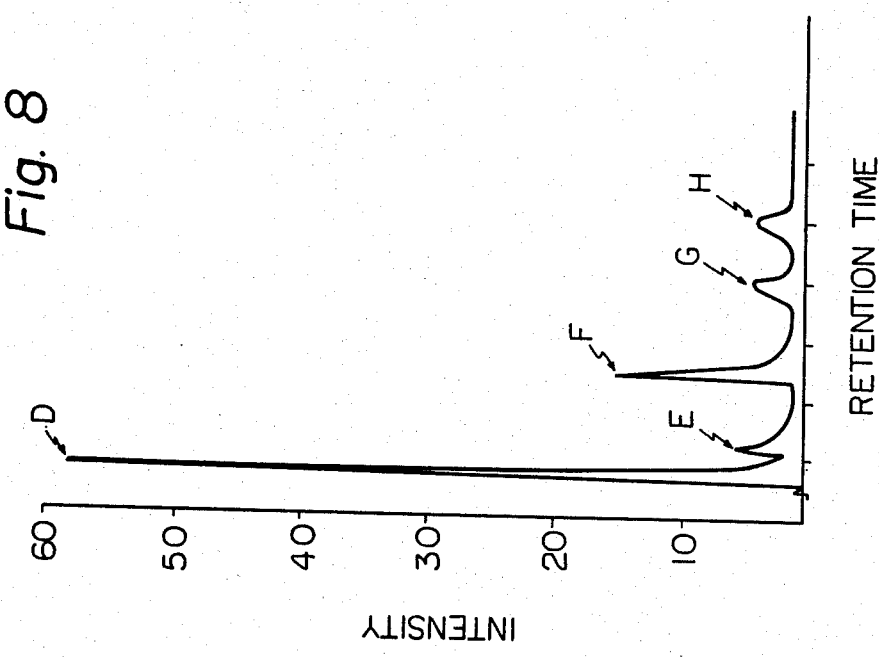
Figure 7:
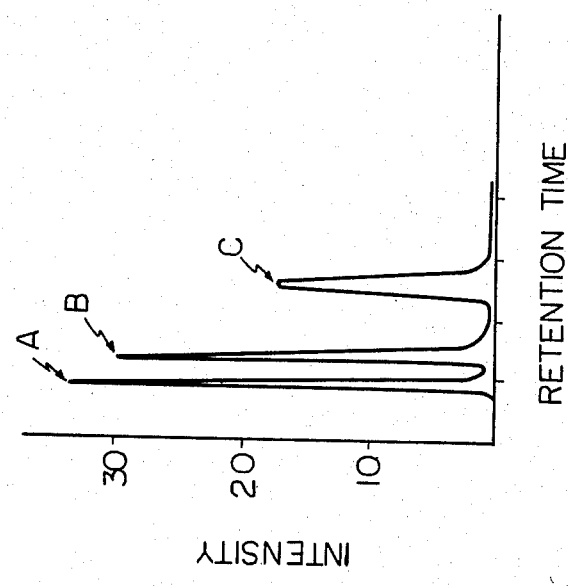

This invention will now be described in detail by reference to the accompanying drawings, in which:

FIG. 1 is a diagram illustrating the state where sugars are separated by using a sheet-like ceramic body for chromatography according to this invention, FIGS. 2 and 3 are diagrams illustrating the state where amino acids are separated by using a sheet-like ceramic body for chromatography according to this invention, FIG. 4 is a diagram illustrating the state where oil soluble dyes are separated by using a sheet-like ceramic body for chromatography according to this invention, FIG. 5 is a diagram illustrating the state where polystyrenes having various molecular weights are separated by using a sheet-like ceramic body for chromatography according to this invention, FIG. 6 is a graph illustrating a relation between the developing distance and the molecular weight in the chromatogram of FIG. 5, FIGS. 7 and 8 are diagrams illustrating results of separation of samples by using a stationary phase carrier for gas chromatography according to this invention.

In this invention, crystalline alumina particles composed mainly of α-$Al_2O_3$ are used as the starting material. Of course, alumina particles composed solely of α-$Al_2O_3$ may be used, but when alumina particles comprising more than 50% by weight, preferably 60 to 80% by weight, of α-$Al_2O_3$ and less than 50% by weight, preferably 20 to 40% by weight, of γ-alumina are used, an optimum separation capacity can be obtained.

Alumina particles having an average particle size smaller than 30μ and a narrow particle size distribution range are preferred. Optimum results can be obtained when alumina particles having a particle size distribution range of from 1 to 10μ are employed.

The ceramic body of this invention can be prepared according to a process comprising molding a composition comprising crystalline alumina particles composed mainly of α-alumina, a resinous binder and a solvent into the form of a sheet, calcining the molded sheet at a temperature of 850° to 1600° C. and, if necessary, pulverizing the calcined sheet into particles.

An acrylic resin or polyvinyl butyral (PVB) is preferably used as the resinous binder. Furthermore, polyvinyl acetate, polyesters and other resinous binders may be used in this invention. Aromatic solvents such as toluene ad xylene, alcohols such as methanol and ethanol, ketones such as acetone and methylethyl ketone and the like can optionally be used as the solvent.

The amount used of the resinous binder is selected so that the obtained sheet is good for the mechanical processing, and the amount used of the solvent is selected so that the surfaces of alumina particles are sufficiently wetted and a flowability necessary for molding is obtained.

The above-mentioned composition is made homogeneous by agitation, kneading or the like, and the homogeneous composition is molded into a predetermined shape, ordinarily a planar shape, for example, a tape or sheet, by tape casting using a doctor blade.

The molded sheet is calcined at a temperature of 850° C. to 1600° C., whereby particles of α-$Al_2O_3$ are partially fused to one another and integrated with one another to obtain a microporous molded body. A preferred calcination temperature differs to some extent depending on the kind of chromatography. For example, in the case of liquid chromatography, a calcination temperature of 1250° to 1400° C. is preferred and in the case of the stationary phase carrier for gas chromatography, a calcination temperature of 1150° to 1400° C. is preferred.

This calcined sheet has a narrow pore size distribution range, and it is preferred that the pore size distribution range be substantially from 0.1 to 10μ.

The obtained calcined and molded sheet is used as a ceramic body for liquid chromatography as it is or after it has been cut in a predetermined size according to need.

This calcined and molded sheet is used as a stationary phase carrier for gas chromatography after it has been pulverized into particles and if necessary, the particle size has been adjusted.

This invention will now be described in detail by reference to the following Examples that by no means limit the scope of the invention.

EXAMPLE 1

Starting α-$Al_2O_3$ particles having the average particle size of 1 to 2μ were used. Then, 100 parts by weight of the starting material was mixed with 8 parts by weight, as the solids, of an acrylic resin and 40 parts by weight of toluene as the solvent. The resulting composition was kneaded and molded into a tape having a thickness of 1 mm by using a doctor blade.

Plates having a size of 1.5 cm × 10 cm were cut from the so molded tape and calcined at 850°, 1285°, 1390° or 1600° C., and the relation between the calcination temperature and the developing speed was examined. Results obtained when n-hexane was used as a developing liquid are shown in Table 1.

TABLE 1

| Run No. | Calcination Temperature (°C.) | Developing Time (min) |
|---|---|---|
| 1 | 850 | 16 |
| 2 | 1285 | 25 |
| 3 | 1390 | 30 |
| 4 | 1600 | 42 |

Note
The developing distance of the solvent was 6.0 cm in each run.

The ceramic body obtained by carrying out calcination at 850° C. showed the shortest developing time, i.e., 16 minutes, among the so-obtained calcined ceramic bodies, but from the viewpoint of the strength of the ceramic body for chromatography, the ceramic body obtained by carrying out calcination at 1285° C. was most preferred. Accordingly, the ceramic body formed by carrying out calcination at 1285° C. was cut into strips and subjected to the experiments described in Examples 2 and 3 given below.

EXAMPLE 2 (Sugars)

D(+)-lactose, D(+)-sucrose and L(−)-sorbose and a mixture thereof were developed with a mixture of water/ethyl acetate/n-propanol (1/35/10 in Volume/Volume ratio) by using the sheet-like ceramic body of Example 1. Coloration was performed by using sulfuric acid. Results obtained were shown in FIG. 1.

In FIG. 1, (a), (b), (c) and (mix) stand for D(+)-lactose, D(+)-sucrose, L(−)-sorbose and mixture thereof respectively.

EXAMPLE 3 (Amino acid)

Results where glycine, D,L-alanine, D,L-valine and L-leucine were developed by using the sheet-like ceramic body of Example 1 were shown in FIG. 2. A mixture of water/ethyl acetate/n-propanol (5/35/10 in volume/volume ratio) was used as developer, and ninhydrin was used for coloration. In FIG. 2 and FIG. 3 as mentioned below, (i), (ii), (iii) and (iv) stand for glycine, D,L-alanine, D,L-valine and L-leucine respectively.

As will be apparent from the foregoing illustration, in this invention, since $\alpha$-$Al_2O_3$ which is very stable and has no substantial adsorbing property is used as the ceramic body for chromatography, substances can be clearly separated based on the difference of the distribution coefficient.

Characteristic properties of the ceramic body for chromatography according to this invention are as follows.

(1) Since $\alpha$-$Al_2O_3$ has a very low activity and is very stable, the ceramic body exerts no substantial adsorbing property, and the ceramic body can be applied to systems to which only liquid-phase chromatography has heretofore been applied.

(2) Large quantities of samples can be separated in a short time very simply.

(3) Since alumina uniform in the particle size is molded by using a binder in the ceramic body of this invention, a uniform thickness can be obtained and the resulting ceramic body is excellent in the separating capacity and reproducibility.

(4) Since calcination is carried out after molding, the mechanical strength is high and deformation is not caused in the ceramic body of this invention.

(5) Desorption can easily be accomplished only by cutting off the portion used for separation and treating it with a solvent capable of dissolving the separated component sufficiently.

(6) Since molding can be performed continuously, the manufacturing cost can be remarkably reduced.

EXAMPLE 4

A sheet-like ceramic body was prepared in the same manner as described in Example 1 except that $\alpha$-$Al_2O_3$ and $\gamma$-$Al_2O_3$ were used in combination at a weight ratio of 75/25 instead of the $\alpha$-$Al_2O_3$ used in Example 1 and calcination was carried out at 1350° C.

Amino acids were separated in the same manner as described in Example 3 by using the so prepared sheet-like ceramic body. Obtained results are shown in FIG. 3, from which it will readily be understood that even in case of substances having a relatively low Rf value D,L-valine, L-leucine, occurrence of the tailing phenomenon could be completely inhibited and each spot was very clear.

EXAMPLE 5 (oil-soluble dyestuff)

A mixture of Indophenol Blue (I), Sudan Red (II) and 4-Dimethylaminoazobenzene (III) was developed with n-hexane by using the ceramic body of Example 4. The results obtained were shown in FIG. 4, from which it will be understood that each spot was very clear and occurrence of the tailing phenomenon could be completely inhibited.

EXAMPLE 6 (polystyrene)

Results where 4 kinds of polystyrene having an average molecular weight ($\overline{Mw}$) of 2,000, 20,000, 160,000 and 1,800,000 respectively were developed with tetrahydrofuran (THF) and ethanol (15:11 in volume ratio) by using the sheet-like ceramic substance were shown in FIG. 5. Iode was used for coloration. The relation between the molecular weight of polystyrene and the developing distance were shown in FIG. 6 from which it will be understood that there is established a linear relation between the developing distance and the molecular weight and that the molecular weight of polymer can be estimated from this relation.

EXAMPLE 7

High-purity alumina ($Al_2O_3$) was molten in an electric furnace and was then solidified. The resulting mass was pulverized and classified to obtain a white corundum crystalline powder having a particle size distribution range of from 0.5 to $80\mu$ and an average particle size of $10\mu$ ($30-1\mu$). Then, 100 parts by weight of the so formed crystalline powder was mixed with 20 to 60 parts by weight (preferably 30 to 50 parts by weight) of toluene as the organic solvent, and the mixture was sufficiently stirred in a pot mill. Then, the mixture was mixed with 4 to 40 parts by weight (preferably 6 to 15 parts by weight) of an acrylic resin as the binder, and the mixture was sufficiently stirred. Then, the mixture was molded into a green ceramic tape having a uniform thickness of 0.2 to 2.0 mm (preferably 0.25 to 1.0 mm) according to the doctor blade method. The green tape was cut into a predetermined size and calcined at 1000° to 1600° C. (preferably 1200° to 1350° C.) to obtain a sheet-like ceramic body having a pore size of 0.1 to $10\mu$. The sheet-like ceramic body was pulverized in a mortar and a fraction of 60 to 80 mesh was collected. Then, 22 g of the so obtained powder was dipped in a solution of 0.7 g of a silicone rubber in 15 cc of tetrahydrofuran (hereinafter referred to as "THF"). THF was evaporated while the mixture was quietly agitated by a spatula, whereby a stationary phase was obtained.

The so prepared stationary phase for gas chromatography was packed in a column having a length of 2 m, and experiments described in Examples 8 and 9 were carried out by using the so prepared packed column.

EXAMPLE 8

A mixture containing benzene, toluene and o-xylene at a volume ratio of 1/1/1 was separated under the following conditions:
Flow rate: 29.2 ml/min
Amount injected: 3 $\mu$l
Column pressure: 0.8 Kg/cm$^2$
Temperature: 130° C.
Carrier gas: nitrogen ($N_2$) gas
Stationary phase liquid: silicone rubber
Detection method: TCD (thermal conductivity detector) method Obtained results are shown in FIG. 8. As will be apparent from the graph of FIG. 8, sharp peaks corresponding to the separated substances were detected, and the presence of benzene, toluene and o-xylene could be clearly confirmed at points A, B and C, respectively.

EXAMPLE 9

A mixture of dioxane, butyl acetate, isobutyl ketone, trans-decalin and cis-decalin was separated under the following conditions:
Flow rate: 30 ml/min
Amount injected: 5 $\mu$l
Column pressure: 0.7 Kg/cm$^2$ Temperature: 130° C.
Carrier gas: nitrogen (N₂) gas
Stationary phase liquid: silicone rubber
Detection method: TCD method Obtained results are shown in FIG. 8. As will be apparent from the graph of FIG. 8, sharp peaks corresponding to the respective substances were observed. More specifically, the presence of dioxane, butyl acetate, isobutyl ketone and cis-decalin could be confirmed at points D, E, F and G, respectively.

It was found that if the pore size exceeds 10μ, separation of the respective components becomes difficult.

As will be apparent from the foregoing illustration, since alumina having a uniform crystal particle size is used for the stationary phase carrier for gas chromatography according to this invention, the stationary phase carrier has no substantial adsorbing property and hence, the tailing phenomenon is not caused to occur at all. Moreover, since the bulk density of the stationary phase carrier alumina of this invention is higher than that of celite customarily used in this field, the time required for packing can be shortened to about 5 minutes (several hours are necessary in case of conventional celite). Moreover, since the stationary phase carrier of this invention is hard and hardly pulverizable, it is not broken or divided when the column is wound in the spiral form. Furthermore, since the stationary phase carrier of this invention is prepared by calcining a molded body having a tape-like shape and pulverizing the calcined body, the pore size distribution range (the range of sizes of pores among crystal particles) is very narrow, that is from 0.1 to 10μ, and therefore, the resulting stationary phase carrier can exert an excellent separating capacity very stably.

What I claim is:

1. A chromatographic process which comprises a sample comprising unknown components in a liquid phase on one end of a solid stationary phase, dipping the end of the solid stationary phase in a developer to separate said unknown components, and analyzing said unknown components, wherein said solid stationary phase is a self-supporting calcined molded porous plate of alumina particles in which the pore size distribution range is from 0.1 to 10μ, and further wherein said plate consists essentially of a mixture of alumina particles containing more than fifty percent weight of α-alumina and less than fifty percent by weight γ-alumina.

2. The process according to claim 1 wherein said plate comprises alumina particles having an average particle size of less than 30μ.

3. The process according to claim 1 wherein said plate has been formed by molding a composition consisting essentially of the alumina particles, a resinous binder and a solvent in the form of a sheet, and calcining the molded sheet at 850° to 1600° C.

4. A chromatographic process comprising dropping an unknown sample on one end of a calcined and molded member consisting essentially of alumina, moving the unknown sample by an appropriate developer and separating respective components of the unknown sample from one another according to differences of the adsorption properties and distribution coefficient among the components of the sample, and wherein the calcined and molded member contains more than fifty percent by weight of α-alumina and has a pore size in the range of from 0.1 to 10μ.

* * * * *